United States Patent [19]

Dye

[11] 4,412,887
[45] Nov. 1, 1983

[54] EVAPORATION PROCESS WITH LIQUID ENTRAINMENT SEPARATION

[75] Inventor: Robert F. Dye, Sugarland, Tex.

[73] Assignee: Shell Oil Company, Houston, Tex.

[21] Appl. No.: 113,141

[22] Filed: Feb. 1, 1980

Related U.S. Application Data

[63] Continuation-in-part of Ser. No. 23,796, Mar. 26, 1979, abandoned.

[51] Int. Cl.³ .............................................. B01D 1/14
[52] U.S. Cl. .................................... 159/47.1; 159/31; 159/DIG. 2; 202/158; 202/197; 202/179; 202/198; 203/40
[58] Field of Search ................... 159/31, 47, DIG. 2; 202/158, 197, 198, 179; 203/40

[56] References Cited

U.S. PATENT DOCUMENTS

| | | | |
|---|---|---|---|
| 3,191,916 | 6/1965 | Kurpit et al. | 202/158 |
| 3,297,566 | 1/1967 | Moyer et al. | 202/197 |
| 3,334,027 | 8/1967 | Goeldner | 203/40 |

*Primary Examiner*—Wilbur L. Bascomb, Jr.
*Attorney, Agent, or Firm*—Richard F. Lemuth

[57] ABSTRACT

An improved evaporation process for accomplishing the separation of a solution into its volatile and non-volatile components. The improvement over conventional evaporation, according to which the solution is fed to a calandria where it is heated and partially vaporized and the resulting calandria vapor stream is subjected to vapor-liquid separation for the removal of entrainment, relates to the practice of an additional and intermediate step in which the calandria vapor is contacted with the feed solution.

11 Claims, 3 Drawing Figures

EVAPORATION PROCESS WITH LIQUID ENTRAINMENT SEPARATION

This application is a continuation-in-part of copending application Ser. No. 23,796, filed Mar. 26, 1979 and now abandoned.

BACKGROUND OF THE INVENTION

This invention relates to a method for increasing the efficiency of the separation of a solution into its volatile and non-volatile components in an evaporator.

It is often desired to separate a solution into its component parts. When the solution is one of an essentially non-volatile material in a volatile solvent, such separation can be carried out in a device commonly known as an evaporator. While there are a large number of evaporator types, all comprise two elements, a calandria and a vapor-liquid separator. Examples of common conventional evaporators are found in Perry's Chemical Engineers' Handbook, fifth edition (1973), at page 11-27. Although they are similar in design to stills and reboilers of distillation columns, evaporators differ in concept in that they do not conventionally comprise trays or packing to promote fractionating contact between vapor and liquid. Since the desired separation in an evaporator is between volatile and non-volatile components, for which the relative volatility of the latter to the former is essentially zero at conditions under which the evaporator is operated, vapor-liquid contact between such components would servo no distillative function.

Each of the calandria and vapor-liquid separator elements of an evaporator accomplishes a degree of separation between volatile and non-volatile components in the feed solution. In the calandria, the solution is heated to take advantage of the volatility differences between the components and effect a primary separation. The major portion of the non-volatile material is withdrawn from the evaporator calandria as a liquid product, which may be either a more highly concentrated solution or a slurry of the non-volatile in a minor portion of the solvent. The major portion of the volatile solvent is withdrawn from the calandria as a vapor stream.

The boiling action within the calandria of an evaporator produces small droplets of liquid, comprising non-volatile at a concentration approximating that in the liquid product, which droplets are carried along with the vapor flow from the calandria. Depending upon the particular circumstances of a given evaporator application, this entrainment of non-volatile into the vapor may represent the loss of a valuable non-volatile material or may result in contamination of the solvent vapor product. When it is considered that the concentration of the non-volatile component in the liquid product is generally many times that in the feed, it is realized that only a very small amount of entrainment of the liquid product has a significantly deleterious effect upon calandria vapor quality. For instance, if the concentration by weight of the non-volatile component in the liquid product is one thousand times its concentration in the evaporator feed, then an entrainment of only one part by weight liquid to one thousand parts vapor would completely negate any separation by the calandria.

In order to produce an evaporator vapor product relatively free of entrainment, the calandria vapor stream is in conventional practice passed to a vapor-liquid separator. Vapor-liquid separators are designed to accomplish removal of a high percentage of the entrained liquid droplets from the calandria vapor by taking advantage of such factors as the difference in density between the vapor and the liquid. Since the quantity of the entrainment is largely a function of vapor flow velocity, the calandria vapor may be passed upward at slow velocity through a large diameter vessel to allow the liquid droplets to settle against the vapor flow by the action of gravity. Cyclone separators and impingement baffles may also be used to coalesce the entrained mist into larger and more easily removed droplets. Wire mesh demister pads are commonly employed for this function, although when the non-volatile component of the liquid solution is a solid under evaporator conditions the pads have a tendency to become fouled and to lose their efficiency. Notwithstanding application of such established techniques of vapor-liquid separation, entrainment is often still a problem and generally the limiting factor in the performance of evaporators with respect to separation of a solution into its volatile and non-volatile components.

SUMMARY OF THE INVENTION

The instant invention provides a method for improving the efficiency of an evaporator in effecting the separation of a liquid solution into its volatile and non-volatile components. According to the invention the overhead vapor flow from the calandria of an evaporator, at a point upstream of vapor-liquid separation, is contacted with the liquid feed solution to the evaporator. The feed solution liquid and calandria overhead vapor are contacted in countercurrent flow over trays, packing material, or the like. Such contact does not, of course, accomplish any distillative function with regard to separation of the feed into volatile and non-volatile components. Nor does it eliminate entrainment of liquid droplets into the vapor stream. However, the vapor-liquid contact does serve to markedly increase the efficiency of the separation accomplished by the evaporator. By means of this contact step, entrained droplets of the evaporator liquid product, highly concentrated with the non-volatile, are removed from the vapor stream leaving the calandria, and droplets of the liquid feed stream are entrained in their place. As a result, the droplets of liquid carried with the vapor stream have a lower concentration of the non-volatile. In effect, the contact step accomplishes dilution of the entrained droplets with respect to their non-volatile content. If sufficient contact surface is supplied, the non-volatile content of the vapor product can be reduced according to the relative proportions of the component in the feed and liquid product steams. In cases in which the concentration of the non-volatile in the feed is relatively low, this reduction can be several orders of magnitude.

The invention thus provides a method for reducing contamination of the evaporator vapor product with the non-volatile to a level not heretofore readily practicable. Unlike conventional practice, the method does not depend upon the increasingly difficult separation of smaller entrained liquid droplets to achieve greater separation efficiency. Rather the improvement associated with the method of the invention functions independently of the relative volatility of the components to be separated and of the factors which influence the physical separation of liquid entrainment from vapor flows.

In addition to facilitating removal of non-volatile from evaporator vapor product, the process of the invention can provide for other advantages in evaporator operation. For instance, the process aids in the prevention of fouling of demister pads with non-volatile. The problems associated with contamination of vapor product through splashing or foaming within the calandria can also be effectively eliminated. Furthermore, application of the method of the invention permits the evaporator to be operated with very high concentrations of non-volatile in the liquid product and thereby promotes maximum volatile solvent recovery.

DESCRIPTION OF THE PREFERRED EMBODIMENTS

Figure 1:
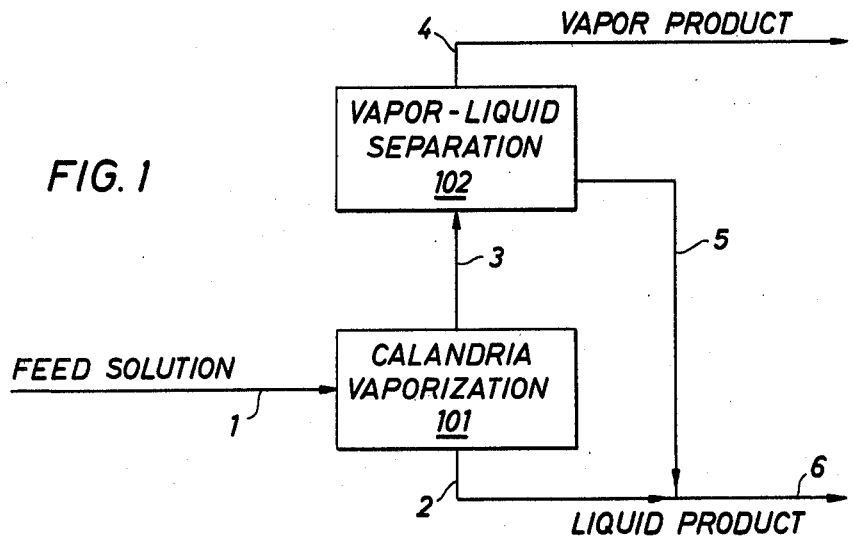

The process of the invention is generally seen as an improvement upon conventional evaporative separation concepts. The improvement is provided by the insertion of a contact step into the conventional process scheme. For the purposes of this invention both the partial vaporization of the volatile component of the feed solution in the calandria and the removal of entrainment in the vapor-liquid separator are considered to be operations familiar to those skilled in the art. These process steps may suitably be performed in any of the numerous types of calandria and separator devices known for evaporator service. Likewise the conditions, such as temperatures and pressures, in the operation of the process of the invention will not substantially differ from those which would suitably be employed in conventional evaporation Processing of the same given feed solution to effect separation of the same volatile and non-volatile components.

The contact step of the process of the invention may conveniently be carried out in any manner which provides intimate contact between vapor and liquid flows. Such contact can suitably be accomplished, for example, in trayed or packed vertical column sections as are commonly employed in distillation, absorption, and similar liquid-gas contact systems. Criteria developed for the application of liquid-gas contact technology in these conventional applications may be likewise employed in the practice of the contact step of the invention. In other words, care should be taken in the design of the contact zone to avoid flooding, priming, excessive entrainment, etc.

Countercurrent flow of the evaporator feed solution and the calandria vapor over sieve trays in a vertical column may generally be expected to give very good contact results for purposes of the invention. It will usually be desirable to employ between 3 and 8 actual trays, or their functional equivalent in packing or the like, although minimal contact over a single tray should afford advantages over the conventional evaporation process practiced without such contact. The optimum design of the contact zone for application in the context of a particular evaporative separation will, of course, be dependent upon the nature of the volatile and non-volatile components of the feed solution, the performance of the calandria and the vapor-liquid separation means, and the desired degree of separation. The appropriate methods for handling such factors for a particular situation may be realized through reference to the general liquid-gas contact art.

Reference is now made to the drawing for illustration of the process of the invention in direct comparison to the conventional evaporation art.

Figure 2:
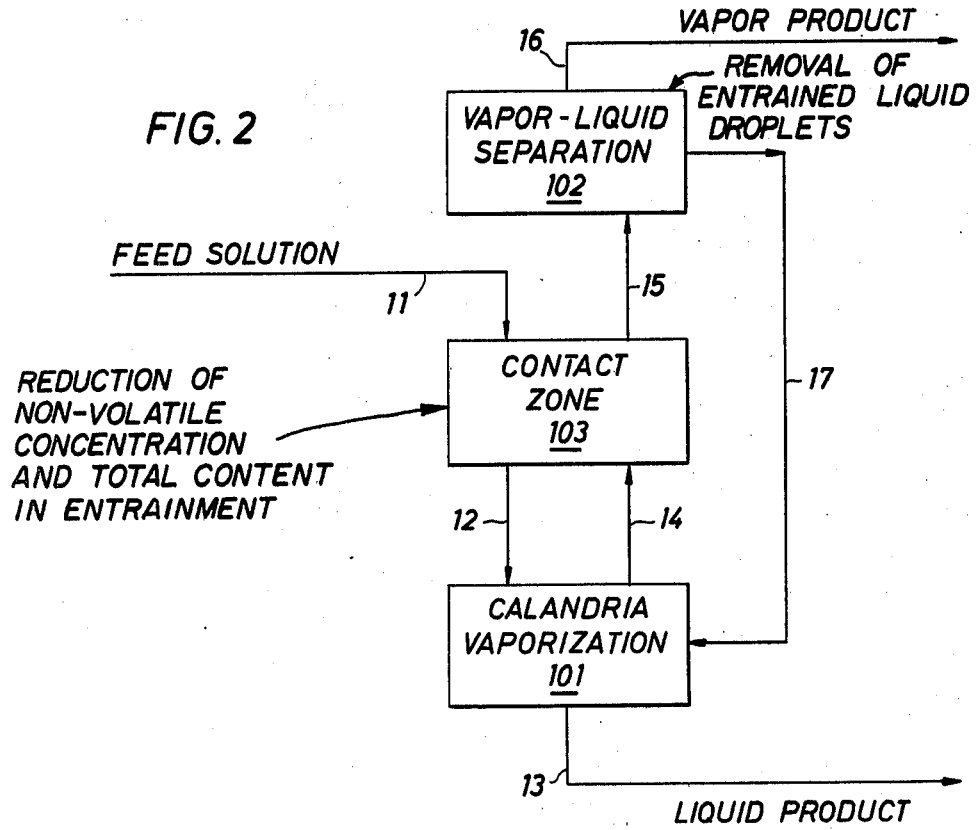

FIG. 1 and FIG. 2 of the drawing are flow diagrams indicating the principal process steps and process flows involved in limited embodiments of conventional evaporation and of the improved process of the invention, respectively.

In FIG. 1 a liquid feed solution, designated stream 1, consisting essentially of a volatile solvent and one or more non-volatile solutes is introduced into a calandria 101 wherein a source of heat (not shown) is applied to effect a primary separation between the volatile and non-volatile components. The major portion of the solvent in the feed is thereby vaporized and passes from the calandria as stream 3, calandria vapor, containing entrained droplets of a liquid rich in the non-volatile. The non-volatile is present in calandria vapor essentially only in the entrained droplets. The remaining portion of the heated feed solution, i.e. that not withdrawn from the calandria as stream 3, is taken as stream 2, calandria bottoms liquid. Vapor stream 3 undergoes a vapor-liquid separation step 102. In the course of vapor-liquid separation, the greater part of the entrained liquid is removed from vapor stream 3 and is then either passed directly via stream 5 to combine with the calandria bottoms liquid 2 to give liquid product 6 as shown, or may alternatively be returned to the calandria. The evaporator liquid product 6 contains a major portion of the non-volatile and a minor portion of the volatile feed solution components. Evaporator vapor product 4, comprises a major portion of the volatile solvent and a minor portion of the non-volatile solute from the feed solution.

FIG. 2 is illustrative of the process of the invention. In addition to the calandria vaporization 101 and the vapor-liquid separation 102 of conventional practice, a contact zone 103 is shown, in which the liquid feed solution, here 11, is contacted with calandria vapor 14. In the same manner as was described with reference to FIG. 1, calandria vapor contains liquid entrainment rich in non-volatile. Non-volatile is present in calandria vapor essentially only in the form of entrainment. In the course of the contact step in contact zone 103, a quantity of the non-volatile-containing entrainment in the calandria vapor is transferred from the calandria vapor into the feed solution 11. Stream 12, comprising liquid feed solution enriched in non-volatile, is withdrawn from the contact zone and passed to the vaporization step 101 where a major portion of the volatile component of the feed solution is vaporized to yield stream 14, calandria vapor. This vapor stream undergoes treatment in contact zone 103 to effect dilution of the liquid entrainment with respect to its non-volatile content. The contact zone overhead vapor 15 passes to vapor-liquid separation 102 for removal of the greater part of the liquid entrainment carried therein. This recovered entrainment 17 is preferably returned to calandria vaporization 101, either directly as shown here or, alternatively, by way of the contact zone as described below with reference to FIG. 3. Return to the calandria is generally preferred, since the entrainment liquid recovered by the vapor-liquid separation step in the process of the invention has a relatively high content of volatile solvent. A vapor product 16, having a non-volatile content substantially less than that of vapor product 4 of FIG. 1, is withdrawn from the vapor-liquid separation means. A liquid product 13, enriched in non-volatile over corresponding stream 6 of FIG. 1, is withdrawn from the calandria.

Figure 3:
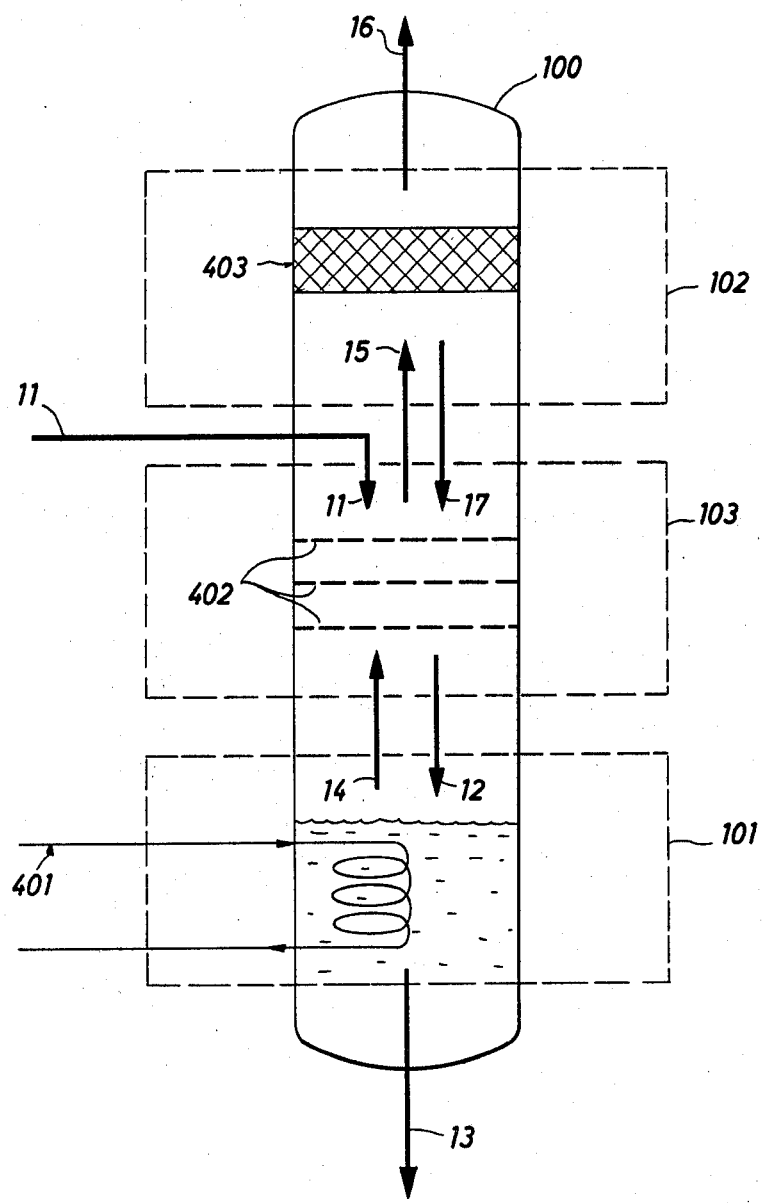

FIG. 3 aids in the description of the process of the invention by depicting the practice of a preferred embodiment in an evaporator adapted for this purpose. It is to be understood that FIG. 3 is presented to more particularly illustrate one mode for practice of the invention and is not intended to limit its greater scope.

Numerical designations applied in FIG. 3 to identify the processing steps and flows correspond to those of FIG. 2. In the process of FIG. 3, a single vertical vessel provides a lower zone wherein the calandria vaporization step 101 of the invention can be performed, an intermediate zone wherein the contact step 103 can be carried out, and an upper zone adapted to accomplish the vapor-liquid separation step 102 of the invention. (The process steps of the invention may, of course, be suitably practiced in like zones contained in multiple vessels.) In the particular process embodiment of FIG. 3, the lower (calandria) zone is shown to receive externally supplied heat through circulation of a heating fluid, for instance steam, in coil 401, the intermediate (contact) zone is shown to comprise three vapor-liquid contact trays 402, and the upper (vapor-liquid separation) zone is shown to have a wire mesh demister pad 403. In operation according to this preferred embodiment of the process of the invention, liquid feed solution 11 is contacted in the contact step 103 with the calandria vapor stream 14 in countercurrent flow over trays 402. In a manner which has been heretofore described, this contact results in a contact zone overhead vapor stream 15 which contains liquid entrainment having a lower non-volatile concentration that that of the calandria vapor stream 14 entering the zone. A contact zone bottoms liquid stream 12 exits the contact zone, falling to the calandria, wherein heat is supplied in the context of the calandria vaporization step 101, to vaporize a volatile stream 14, containing some non-volatile essentially in the form of entrainment, which rises to the contact zone. A portion of the liquid mixture of volatile and non-volatile components in the calandria is withdrawn as calandria bottoms liquid stream 13 which is the process liquid product. Contact zone overhead vapor 15 rises to the vapor-liquid separation means, here demister pad 403, which functions to separate from the vapor, for purposes of vapor-liquid separation step 102, the greater part of the entrained liquid therein to yield the process vapor product 16 and the recovered liquid entrainment stream 17. As has been noted, stream 17 may be routed to the calandria or, alternatively, directly to the bottoms product stream. In the preferred embodiment illustrated in FIG. 3, this recovered liquid entraiment stream, comprising droplets coalesced by the demister pad 403, is permitted to fall from the pad and return to the calandria through or by way of the contact zone. Because entrainment stream 17 is generally of low flowrate relative to the feed liquid 11, and further because this recovered entrainment has a relatively low concentration of non-volatile, having been separated from a calandria vapor stream which was itself subjected to contact with feed liquid according to the invention, its return to the calandria by way of the contact zone has little if any adverse influence upon the performance of vapor-liquid contact in the zone. In fact, in some instances, a slight increase in total liquid flow in the contact zone attributable to return therethrough of liquid stream 17 may result in improved vapor-liquid contact step for purposes of the invention. And furthermore, return of recovered entrainment stream 17 to the calandria in the manner illustrated can be seen to have advantages in simplicity of operation when the vapor-liquid separation means is physically located above the contact zone, and particularly when the contact step and the vapor-liquid separation step of the invention are carried out within a single vessel, as is the case in the embodiment of the process depicted in FIG. 3.

Since the primary purpose of the contact step in the evaporation process is to effect dilution of the non-volatile components present in the entraiment carried into the vapor flow, it is to be understood that in the practice of the invention the contact zone overhead vapor stream comprises less total entrained non-volatile than the calandria vapor stream which enters the contact zone. However, it is not necessary for the vapor leaving the contact zone to contain a lesser quantity of liquid entrainment than that vapor entering the zone. In other words, the primary function of the contact zone relates to dilution of entrainment with respect to non-volatile content and not to vapor-liquid separation, which is more efficiently accomplished through the following process step particularly directed to this separation. Nevertheless, there are obvious advantages to be realized through practice of the contact step in a manner which minimizes the total liquid entrainment leaving the contact zone. To this end it is desirable to employ sieve trays in the contact zone, as their use is known in the art to generally provide less entrainment of tray liquid into the vapor flow than is the case with many other tray types.

Feed solutions which are suitably processed according to the invention are of the same nature as those heretofore separated by conventional separation techniques. As will be understood by the skilled artisan, evaporation processes are conventionally applied to feed solutions which consist essentially of one or more non-volatile components present in liquid solution in a volatile solvent. Ideally, the feed solution contains no components other than the stated volatile and non-volatile components. However, in actual practice, evaporator feed solutions consist of these volatile solvent and non-volatile solute components, as well as of inconsequential quantities of other substances, which are considered merely as impurities ordinarily associated with the feed solution and, after evaporation processing, with the vapor and liquid product thereof.

Distinction is drawn between distillative and evaporative separation techniques, along conventional lines, according to the relative volatilities of the volatile and non-volatile components which it is desired to separate. For purposes of such distinction, it is to be understood herein that the relative volatility of the volatile solvent to the non-volatile solute components of the feed solution is at least 1000 to 1, preferably 10,000 to 1 and most preferably 1,000,000 to 1, at the operating conditions of the contact zone. Accordingly, the relationship between volatile and non-volatile materials, as the terms are used herein to describe the invention, provides a relative, and not an absolute, distinction between their inherent volatility properties. When a liquid solution, containing a volatile solvent and non-volatile solute components for which the relative volatility relationship is as specified is heated to vaporize the major portion of the solvent, then the solute components will be present in the resulting solvent essentially only in entrained liquid droplets. This is a critical feature of evaporation as the process is herein defined. Examples of suitable feed solutions include solutions of many inorganic salts in water and many solutions of organic salts in common organic solvents such as aldehydes, ketones, and alcohols or in boiling range solvents such as naphtha or kerosene.

The process of the invention has specific utility in accomplishing the evaporative separation of volatile polyhydric alcohols, particularly ethylene glycol, diethylene glycol and triethylene glycol, from mixtures also comprising moderately soluble, essentially non-volatile inorganic and organic salts, e.g., carbonates, acetates, and formates. Such mixtures are commonly produced, for example, as by-product in the manufacture of ethylene oxide, in which case the mixtures may also contain small amounts of other organic compounds and significant quantities of water. The improved evaporation process of the invention offers significant advantages in the separation of the volatile and non-volatile components of such mixtures over that accomplished through conventional evaporation practice.

In addition to a liquid feed solution of non-volatile in a volatile solvent, it is common in evaporator operation for the feed material to also comprise a separate vapor and/or a solid phase, and in some cases a second liquid phase. Under most applications, the performance of the process of the invention will not be adversely influenced by the extraneous phases which accompany the liquid feed solution as it enters the contact zone. However, caution should be taken to assure that any solids in the feed material are not in such form or quantity as would lead to fouling of the contact media.

Likewise, it is common for the stream which is herein termed the liquid product to contain non-volatiles both in solution and as solids in suspension. Crystallizing evaporators, for example, are designed to yield a slurry product. The process of the invention may generally be expected to be suitable for such service. As has been heretofore noted, the invention may in fact be preferred in these applications as a means of preventing fouling of the vapor-liquid separation means. For convenience, the liquid product terminology used herein is intended to encompass both a single- or multi- phase liquid solution and a suspension of solid particulate in a liquid phase.

The evaporation process of the invention is of particular advantage when applied to the separation of multiple feed streams of different composition in a single operation. In such a situation, the several feed streams may be fed to different stages of the contact zone according to their concentration of non-volatile. Thus, for example, as the vapor flows from the calandria to the vapor-liquid separator, it contacts the liquid feed stream of highest non-volatile concentration first and that of lowest concentration last. Even greater degrees of solvent/solute separation may be obtained, of course, when in the context of the process of the invention a liquid solvent stream, free of solute, is contacted with the vapor following its contact with all of the evaporator feed streams but prior to vapor-liquid separation. Such practice, however, necessitates increases in evaporator equipment size, heat input, etc.

The invention is further illustrated by means of the following example:

EXAMPLE

This example illustrates the benefits which may be realized when a narrow preferred embodiment of the process according to the invention is applied to the evaporative separation of a volatile solvent from a solution consisting of the solvent and one or more non-volatile components. For purposes of this example, the relative volatility of non-volatiles to the solvent is essentially zero under evaporator operating conditions. The performance of the improved process of the invention is compared with conventional evaporation practice with respect to the non-volatile impurities carried over into the solvent vapor product and with respect to the quantity of non-volatiles recovered in the liquid product. Reference is made herein to FIGS. 1 and 2 of the drawing to further identify each of the various process streams.

First, the performance of a conventional evaporation process is described. In a typical conventional process (FIG. 1), 9000 lb/hr of a single liquid feed solution (1) consisting of 8400 lb/hr of a volatile solvent and 600 lb/hr of a non-volatile solute (a 14:1 volatile to non-volatile ratio) is continuously introduced into a calandria (101) which is designed to yield 600 lb/hr of a calandria bottoms liquid (2), containing 200 lb/hr of the solvent and 400 lb/hr of the non-volatile, and 8400 lb/hr of a crude calandria vapor stream (3) containing 8100 lb/hr of solvent vapor, zero lb/hr non-volatile vapor, and 300 lb/hr liquid entrainment. The liquid entrained in the calandria vapor in this conventional operation would have approximately the same composition as the calandria bottoms liquid product and thus be made up of 100 lb/hr solvent and 200 lb/hr non-volatile. The calandria vapor stream (3) is immediately passed to a vapor-liquid separator (102) designed to effect removal of 99 percent of the liquid entrainment. The finished vapor product (4) withdrawn from the separator would then be composed of 8100 lb/hr solvent vapor and 3 lb/hr entrained liquid of which 1 lb/hr is solvent and 2 lb/hr is the non-volatile solute. It is calculated that the finished vapor product thus comprises a total of 247 ppm by weight of the non-volatile. After its removal from the calandria vapor stream by the vapor-liquid separator, 297 lb/hr of liquid entrainment having essentially the same concentration of non-volatile in volatile solvent as does the liquid product may be routed (via 5) directly to liquid product (2).

The evaporation process according to the invention (FIG. 2) is next applied to accomplish separation of a liquid feed solution (here 11) of the same composition and flowrate noted above, utilizing the same calandria and the same vapor-liquid separation equipment operated under the same conditions of temperature and pressure and with the same heat input. A crude calandria vapor stream 14 would be obtained, which in the process of the invention is then routed to a contact zone where it is contacted in countercurrent flow with the feed solution over a number of sieve trays sufficient to yield a vapor stream 15 containing entrained liquid droplets of a non-volatile concentration essentially the same as that of the feed solution. Here, the contact zone is designed in such a manner that the vapor flow (15) from the contact zone to the vapor liquid separator again contains 300 lb/hr entrainment. The addition of the contact step according to the improved process of the invention thus does not in this instance reduce the quantity of entrainment entering the separator. However, the relative proportions of the solvent and non-volatile in this entrainment would correspond closely to the feed solution composition and not to the composition of the calandria liquid product. Consequently, the 300 lb/hr of entrainment would be composed of approximately 14 parts solvent to one part non-volatile, or, in other words, of 280 lb/hr solvent and 20 lb/hr non-volatile. Following the vapor-liquid separation step, in which 99% of the liquid entrainment is again removed, the finished vapor product (16) would contain 8,100 lb/hr solvent vapor and a liquid entrainment consisting of 2.8 lb/hr solvent and 0.2 lb/hr non-volatile. It is calculated that the finished vapor product comprises only 24.7 ppm by weight of the non-volatile.

A ten-fold decrease in the carry-over of non-volatile into the vapor product is thus illustrated for practice of the evaporation process according to the improved process of the invention. In addition the liquid product (13) resulting from practice of the process of the invention contains 1.8 lb/hr more of the non-volatile than did the liquid product obtained through the conventional evaporator operation. Although the comparison afforded by this example implicitly overlooks certain secondary effects which influence the performance of such a process, for instance the effects on vapor-liquid separator efficiency of different entrained liquid properties such as density and droplet size, it is clear that the process of the invention provides significant improvement over conventional practice.

While the invention in effect specifies the addition of a contact step to the conventional method for evaporative separation, it is seen to provide simplification of the overall process. For instance, precautions heretofore conventionally taken in the design of calandrias to control excessive entrainment, splashing and foaming may prove unnecessary, as both continuous and intermittent problems of this sort can be effectively controlled by the contact zone. Likewise, it will be possible under practice of the invention to significantly relax the performance specifications of the vapor-liquid separation means and still achieve a relatively high degree of separation.

Through practice of the invention, entrainment of non-volatile into the calandria vapor product is effectively minimized in a manner that does not rely upon the more difficult and costly removal of smaller liquid droplets. Furthermore, although the contact step constitutes an addition to conventional evaporation processes, it functions without the need of additional evaporator manual monitoring or operation or automatic instrumentation or controls.

I claim as my invention:

1. An improved evaporation method for the separation of a liquid feed solution consisting essentially of volatile solvent and non-volatile solute components having a relative volatility of at least 1000 to 1 into a vapor product containing a major portion of the volatile solvent and a minor portion of the non-volatile solute, said minor portion of non-volatile present in the vapor product essentially only in entrained liquid droplets, and a liquid product containing a minor portion of the volatile solvent and a major portion of the non-volatile solute, which comprises
   (a) heating in a calandria a liquid solution consisting essentially of a volatile solvent and the non-volatile solute to produce a calandria vapor stream containing solvent vapor and entrained liquid droplets and a calandria bottoms liquid stream which is the liquid product, said calandria vapor stream containing non-volatile solute essentially only in the entrained droplets;
   (b) contacting, in countercurrent flow in a contact zone containing as a contact media packing or one or more trays, the liquid feed solution with the calandria vapor stream to yield a contact zone overhead vapor stream containing solvent vapor and entrained liquid droplets and a contact zone bottoms liquid, said liquid droplets entrained in the contact zone overhead vapor having a lower concentration of non-volatile solute than the droplets entrained in the calandria vapor, and said contact zone overhead vapor comprising a lesser total quantity of non-volatile than does the calandria vapor;
   (c) separating, in a vapor-liquid separation means, the greater part of the entrained liquid from the contact zone overhead vapor to produce the vapor product and a recovered liquid entrainment stream;
   (d) introducing both the contact zone bottoms liquid stream from (b) and the recovered liquid entrainment stream from (c) into the calandria as the liquid solution to be heated according to (a).

2. An improved evaporation method for the separation of a liquid feed solution consisting essentially of volatile solvent and non-volatile solute components having a relative volatility of at least 1000 to 1 into a vapor product containing a major portion of the volatile solvent and a minor portion of the non-volatile solute, said minor portion of non-volatile present in the vapor product essentially only in entrained liquid droplets, and a liquid product containing a minor portion of the volatile solvent and a major portion of the non-volatile solute, which comprises
   (a) heating in a calandria a liquid solution of the volatile solvent and the non-volatile solute to produce a calandria vapor stream containing solvent vapor and entrained liquid droplets and a calandria bottoms liquid stream, said calandria vapor stream containing non-volatile solute essentially only in the entrained droplets;
   (b) contacting, in countercurrent flow in a contact zone containing as a contact media packing or one or more trays, the liquid feed solution with the calandria vapor stream to yield a contact zone overhead vapor stream containing solvent vapor and entrained liquid droplets and a contact zone bottoms liquid, said liquid droplets entrained in the contact zone overhead vapor having a lower concentration of non-volatile solute than the droplets entrained in the calandria overhead vapor, and said contact zone overhead vapor comprising a lesser total quantity of non-volatile than does the calandria vapor;
   (c) separating, in a vapor-liquid separation means, the greater part of the entrained liquid from the contact zone overhead vapor to produce the vapor product and a recovered liquid entrainment stream;
   (d) introducing the contact zone bottoms liquid stream from (b) into the calandria as the liquid solution to be heated according to (a);
   (e) combining the calandria bottoms liquid stream from (b) and the recovered liquid entrainment stream from (c) to yield the liquid product.

3. The process of either of claims 1 or 2, wherein the relative volatility of the volatile solvent to each of the non-volatile solute components is at least 10,000 to 1.

4. The process of claim 3 wherein the relative volatility is at least 1,000,000 to 1.

5. The process of either of claims 1 or 2, wherein the contact zone contains sieve trays as contact media.

6. The process of either of claims 1 or 2, wherein the contact zone contains between 3 and 8 trays, inclusive.

7. The process of claim 1 wherein the liquid feed solution comprises a volatile solvent containing water and polyhydric alcohols and a non-volatile solute containing organic and inorganic salts.

8. The process of claim 2 wherein the liquid feed solution comprises a volatile solvent containing water and polyhydric alcohols and a non-volatile solute containing organic and inorganic salts.

9. The process of claim 1, wherein the recovered liquid entrainment stream from (c) is passed through the contact zone before it is introduced into the calandria in (d).

10. The process of claim 9, wherein the recovered liquid entrainment stream falls by gravity flow from the vapor-liquid separation means to the calandria by way of the contact zone.

11. The process of claim 10, wherein the contact zone and vapor-liquid separation means are contained within a single vessel.

* * * * *